United States Patent [19]

Ryaby et al.

[11] 4,315,503
[45] Feb. 16, 1982

[54] MODIFICATION OF THE GROWTH, REPAIR AND MAINTENANCE BEHAVIOR OF LIVING TISSUES AND CELLS BY A SPECIFIC AND SELECTIVE CHANGE IN ELECTRICAL ENVIRONMENT

[75] Inventors: John P. Ryaby, Essex Fells; Arthur A. Pilla, Wyckoff, both of N.J.

[73] Assignee: Electro-Biology, Inc., Fairfield, N.J.

[21] Appl. No.: 100,291

[22] Filed: Dec. 5, 1979

Related U.S. Application Data

[63] Continuation of Ser. No. 927,758, Jul. 25, 1978, abandoned, which is a continuation-in-part of Ser. No. 742,706, Nov. 17, 1976, Pat. No. 4,105,017, which is a continuation-in-part of Ser. No. 633,408, Nov. 19, 1975, abandoned.

[51] Int. Cl.³ ............................................. A61N 1/40
[52] U.S. Cl. ................................. 128/1.5; 128/82.1; 128/419 F; 128/421
[58] Field of Search .................... 128/1.3, 1.5, 419 F, 128/419 R, 420 R, 421–423, 783, 803, 804

[56] References Cited

U.S. PATENT DOCUMENTS

| | | | |
|---|---|---|---|
| 2,830,578 | 4/1958 | DeGroff | 128/419 R |
| 3,127,895 | 4/1964 | Kendall et al. | 128/422 |
| 3,890,953 | 6/1975 | Kraus et al. | 128/1.5 |
| 3,893,462 | 7/1975 | Manning | 128/1.5 |
| 3,915,151 | 10/1975 | Kraus | 128/1.5 |
| 3,952,751 | 4/1976 | Yarger | 128/422 |

FOREIGN PATENT DOCUMENTS 497021  4/1976  U.S.S.R. .................... 12B/419 F

OTHER PUBLICATIONS

Bassett et al., "A Non–Operative . . . Electromagnetic Fields", Clin. Orth., May 1977, vol. 124, p. 128–143.
Bassett et al., "Augmentation of Bone Repair . . . ", Science, vol. 184, p. 575–577, May 3, 1974.

*Primary Examiner*—Lee S. Cohen
*Attorney, Agent, or Firm*—Hopgood, Calimafde, Kalil, Blaustein & Judlowe

[57] ABSTRACT

Surgically non-invasive method of and apparatus for altering the growth, repair and maintenance behavior of living tissues and/or cells by inducing voltage and concomitant current pulses of specific time-frequency-amplitude relations therewithin.

28 Claims, 13 Drawing Figures

MODIFICATION OF THE GROWTH, REPAIR AND MAINTENANCE BEHAVIOR OF LIVING TISSUES AND CELLS BY A SPECIFIC AND SELECTIVE CHANGE IN ELECTRICAL ENVIRONMENT

CROSS REFERENCE

This is a continuation of copending application Ser. No. 927,758, filed July 25, 1978, now abandoned, which in turn is a continuation-in-part of Ser. No. 742,706, filed Nov. 17, 1976, now U.S. Pat. No. 4,105,017, which was a continuation-in-part of Ser. No. 633,408, filed Nov. 19, 1975, now abandoned.

BACKGROUND AND BRIEF DESCRIPTION OF THE INVENTION

This invention relates to the treatment of living tissues and/or cells by altering their interaction with the charged species in their environment. In particular, the invention relates to a controlled modification of cellular and/or tissue growth, repair and maintenance behavior by the application of encoded electrical information. Still more particularly, this invention provides for the application by a surgically non-invasive direct inductive coupling, of one or more electrical voltage and concomitant current signals conforming to a highly specific pattern.

Several attempts have been made in the past to elicit a response of living tissue to electrical signals.

Investigations have been conducted involving the use of direct current, alternating current, and pulsed signals of single and double polarity. Invasive treatments involving the use of implanted electrodes have been followed, as well as non-invasive techniques utilizing electrostatic and electromagnetic fields. Much of the prior work that has been done is described in Volume 238 of the *Annals of The New York Academy of Sciences* published Oct. 11, 1974 and entitled "Electrically Mediated Growth Mechanisms in Living Systems" (editors A. R. Liboff and R. A. Rinaldi). See also "Augmentation of Bone Repair by Inductively Coupled Electromagnetic Fields" by C. Andrew L. Bassett, Robert J. Pawluk and Arthur A. Pilla published in Volume 184, pages 575-577 of *Science* (May 3, 1974).

The invention herein is based upon basic cellular studies and analyses which involve a detailed consideration of the interactions of charged species, such as divalent cations and hormones at a cell's interfaces and junctions.

Basically, it has been established that, by changing the electrical and/or electrochemical environment of a living cell and/or tissue, a modification, often a beneficial therapeutic effect, of the growth, repair and maintenance behavior of said tissue and/or cells can be achieved. This modification or effect is carried out by subjecting the desired area of tissues and/or cells to a specifically encoded electrical voltage and concomitant current, whereby the interactions of charged species at the cell's surfaces are modified. Such modifications engender a change in the state or function of the cell or tissue which may result in a beneficial influence on the treated site. For example, in the specific case of bone growth and repair, it is possible with one electrical code, hereinafter referred to as Mode 1, to change the interaction of the ion such as $Ca^{2+}$ with a cell's membranes. Whereas, with another electrical code, hereinafer referred to as Mode 2, a modification in the same cell's protein-synthesis capabilities can be affected.

For example, tissue-culture experiments involving the study of embryonic chick-limp rudiments show that the use of a Mode 1 code signal elicits enchanced $Ca^{2+}$ release of up to 50% from the competent osteogenic cell. This effect is highly specific to the parameters of the electrical code of Mode 1. Thus, this code influences one major step of ossification, i.e., the mineralization of a bone-growth site. Similar tissue-culture studies using Mode 2 code signals have demonstrated that this code is responsible for enhanced protein production from similar competent osteogenic cells. This latter effect is also highly specific to the parameters of the electrical code of Mode 2. In other words, this code affects certain metabolic processes for these types of cells such as those involved in calcium uptake or release from mitochrondria as well as the synthesis of collagen, a basic structural protein of bone.

These studies show that the electrical codes of Mode 1 and Mode 2 elicit individual tissue and cellular responses, indicating that each code contains a highly specific informational content therein. Based upon these and other studies, it has been possible to utilize Mode 1 or Mode 2 signals or a particular combination of Mode 1 and Mode 2 signals to achieve a specific response required to enable the functional healing of a bone disorder. These electrical modes have been applied successfully to human and animal patients for non-healing fractures such as congenital pseudarthrosis and nonunions as well as fresh fractures. Successes achieved in the congenital pseudarthrosis cases are particularly noteworthy, since normally 80% of children thus afflicted require amputation, since conventional treatments such as bone grafting and internal fixation are unsuccessful.

While there have been many investigations in the past of the response of living tissues and/or cells to electrical signals, clinical results to date using prior techniques have not been uniformly successful or generally accepted within the appropriate professional community. Several reasons contribute to this state. First, it has not been realized heretofore that electrical signals of very specific informational content are required to achieve a specifically desired beneficial clinical effect on tissue and/or cells. Second, most of the prior techniques utilize implanted electrodes, which by virtue of unavoidable faradaic (electrolysis) effects are often more toxic than beneficial in the treated site. Furthermore, the cells and/or tissues are subjected to a highly uncontrolled current and/or voltage distribution, thereby compromising the ability of the cells to respond, should they do so, to the applied signal. This highly uncontrolled current and/or voltage distribution also applies in the case of capacitatively coupled signals.

In contrast, the surgically non-invasive direct inductive coupling of electrical informational content of specific electrical codes as involved in the present invention produces within living tissue and/or cells a *controlled* response.

In brief, the present invention involves the recognition that the growth, repair and maintenance behavior of living tissues and/or cells can be modified beneficially by the application thereto of a specific electrical information. This is achieved by applying pulse waveforms of voltage and concomitant current of specific time-frequency-amplitude relations to tissue and/or cells by a surgically non-invasive means through use of a varying electromagnetic field which is inductively coupled through direct induction into or upon the tissue and/or cells under treatment. The information furnished to the cells and/or tissues by these signals is designed to influence the behavior of non-excitable cells such as those involved in tissue growth, repair, and maintenance. These growth, repair and maintenance phenomena are substantially different from those involved in excitable cellular activity (e.g., nerves, muscles, etc.), particularly with respect to the type of perturbation required. Thus, the voltages and concomitant currents impressed on the cells and/or tissues are at least three orders of magnitude lower than those required to effect cellular activities such as cardiac pacing, bladder control, etc.

The invention will be more completely understood by reference to the following detailed description, in conjunction with the accompanying drawings, in which:

FIGS. 7 to 11 are electrical diagrams to illustrate further forms and employments of the invention.

DETAILED DESCRIPTION

Figure 1:
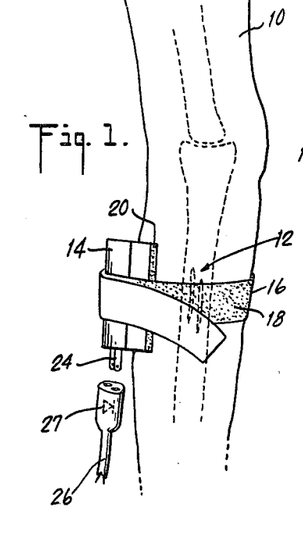
FIG. 1 is a simplified view showing the treatment of a bone in accordance with the invention.
Figure 2:
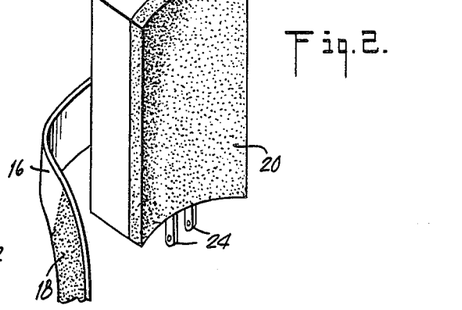
FIG. 2 is a perspective view of the treatment unit shown in FIG. 1.
Figure 3:
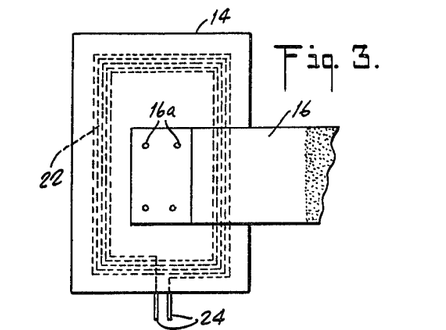
FIG. 3 is a view (from the rear) of the unit shown in FIG. 2, showing the positioning of a coil therein used for treatment purposes.

Referring to FIGS. 1 to 3, the leg 10 of a person having a broken bone, as indicated as at 12, is shown as representative of the application of the invention to the stimulation of bone growth for healing purposes. A treatment head 14 is positioned outside the skin of the person, and is held in place by use of a strap 16 (secured to head 14 by fasteners 16a) which may include Velcro* material 18 thereon so that the strap may be wrapped about the leg and about the treatment head to maintain the treatment head in position against the leg. The treatment head 14 may include a foam material 20 on the inside surface thereof for the purpose of cushioning and ventilating the treatment head against the leg. It will be noted that the treatment head 14 is generally curved on the interior surface thereof so that it conforms to the shape of the leg under treatment.

*Velcro is a trademark of American Velcro, Inc., for its hook-and-loop fastener material.

The treatment head 14 includes therein a coil 22 which may be of any suitable shape. As shown in FIG. 3 the coil 22 is generally rectangular in shape so as to define a "window" within the interior portion of the turns of the coil. The coil 22 may lie in a plane or it may generally be curved to conform to the curvature of the treatment head 14. The coil 22 includes terminals 24 which extend away from the treatment head 14 to be coupled to a cable 26 for connection to a suitable energizing circuit, as will be explained below in more detail. A diode 27 may be included within the cable 26 for connection across the coil 22 as will also be explained below.

The treatment head 14 is positioned on the patient so that the "window" formed by the coil 22 is adjacent the break 12, i.e., adjacent the tissue under treatment. The coil 22 is energized, as will be explained in more detail below, and induces an electrical potential within the tissue under treatment. It has been found that a particular type of signal should be induced within the tissue and this is achieved by energizing the coil 22 by a circuit, such as shown in FIG. 4 or FIG. 5, to produce the pulse signal shown in FIG. 5a or FIG. 5b.

Figure 4:
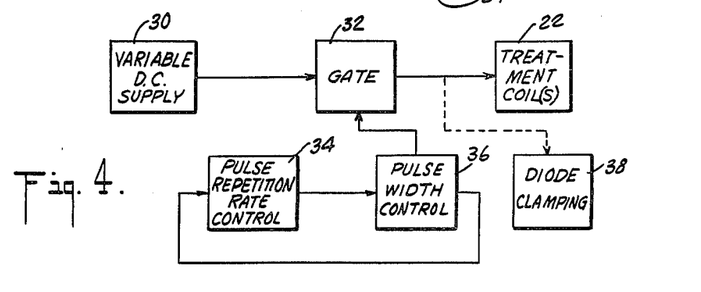
FIG. 4 is a block diagram of an electrical system for energizing the coil shown in FIG. 3 for Mode 1 treatment.
Figure 5:
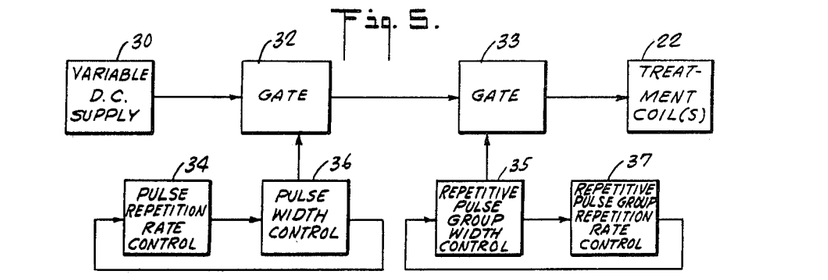
FIG. 5 is a block diagram of an electrical system for energizing the coil shown in FIG. 3 for Mode 2 treatment.
Figure 5A:
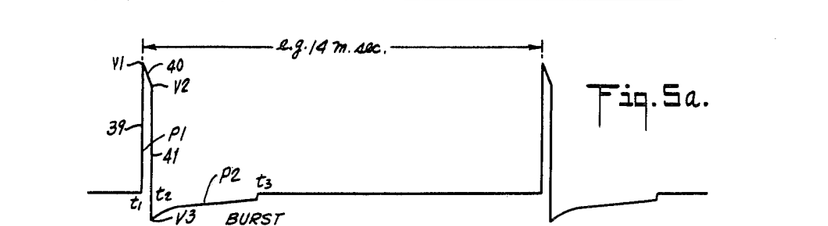
FIG. 5a and 5b are pulse waveform diagrams for Mode 1 and Mode 2 treatments, respectively, showing presently preferred pulses as induced in living tissues and cells.

Referring to FIG. 4, a variable dc supply 30 is coupled through a gate 32 to the treatment coil 22 (or coils, as the case may be, and as explained in greater detail in our copending application Ser. No. 887,485, filed Mar. 17, 1978). The gate 32 is under the control of control units 34 and 36 which cause a pulse signal consisting of repetitive pulses of electrical potential to be applied to the treatment coil 22. Each pulse, as shown in FIG. 5a, is composed of a "positive" pulse portion P1 followed by "negative" pulse portion P2 because of the stored electrical energy within the treatment coil. In the circuit of FIG. 4, a diode clamping unit 38 may be employed to limit the peak potential of that negative pulse portion. The diode clamping unit 38 may be one or more diodes connected across the coil 22, and may be advantageously located within the cable 26. The diode 27 shown in FIG. 1 constitutes such a clamping unit 38.

In FIG. 5a, the signals at the treatment coil 22 and hence the induced signal within the tissue to be treated are shown. At time $t_1$, it is assumed that gate 32 is gated on by an appropriate signal from control unit 36 (designated a pulse width control unit) so that the electrical potential across the treatment coil 22 is raised from about zero volts along pulse segment 39 to a potential designated v1 in FIG. 5a. The signal across the treatment coil decays in a second pulse segment along the portion of the curve designated 40 in FIG. 5a. The slope of that curve is determined by the L/R time constant of the circuit of FIG. 4, i.e., the inductance of the treatment coil and the effective resistance of the circuit, including distributed factors of capacitance, inductance and resistance. For treatment of many tissues and cells, it is believed desirable to adjust the circuit parameters so that the portion 40 of the curve is as flat as possible, rendering the signal applied to the treatment coil 22 as rectangular in shape as possible. At the time $t_2$, the gate 32 is gated off by the control unit 36. Just prior to being gated off, the signal across the treatment coil is at the potential v2 shown in FIG. 5a. The potential across the treatment coil drops from the level v2 in a third pulse segment 41 to a potential of opposite polarity designated v3 in FIG. 5a. The magnitude of the opposite polarity potential v3 may be limited by the diode clamping unit 38 to a relatively small value as compared with value v1. The signal across the treatment coil 22 then decays from the potential level v3 to the zero or reference potential level, finally effectively reaching that level at time $t_3$. A predetermined period passes before the pulse-repetition rate control unit 34 generates an appropriate timing signal to trigger the control unit 36 to generate a signal to turn gate 32 on again to continue the cycle just explained.

The control units may typically be monostable multivibrators, e.g., to generate appropriate timing signals and which may be variable to control pulse duration and repetition rate within desired limits. Further, the use of a variable dc supply 30 permits variation of the amplitude of the pulse signal as desired.

Figure 5B:
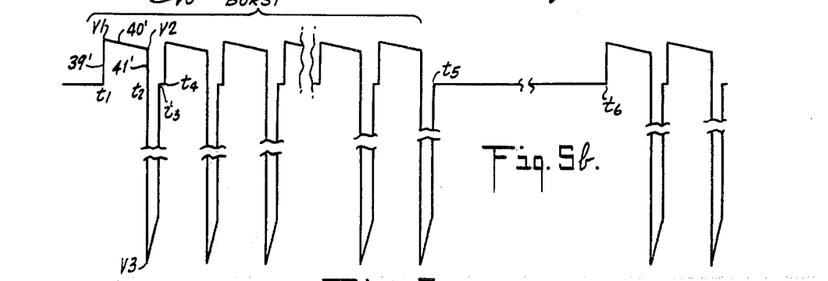

When pulse-train operation (Mode 2) is employed, additional timing circuitry similar to units 34 and 36 in FIG. 4 is employed to provide the burst-segment width and the burst-segment repetition rate. Referring to FIG. 5, control units 35 and 37 control gate 33 to produce a signal applied to coil(s) 22 of the waveform type as shown in FIG. 5b. The circuit is otherwise the same as in FIG. 4, except that the diode-clamping unit 38 is omitted to permit the large negative-pulse portions as shown in FIG. 5b. The control units 35 and 37 determine the number of pulses in a burst and the time between successive bursts.

It has been found that the signal across the treatment coil 22, and hence the induced signal within the tissue under treatment, should satisfy certain criteria. These criteria will be specified with respect to the signal *as induced in the tissue and/or cells under treatment.* Such induced signal may be monitored, if desired, by use of an auxiliary monitoring pickup coil (not shown) which is positioned at a distance from the treatment coil 22 corresponding to the distance of the tissue under treatment from that coil, as will be explained in more detail below. In any event, it has been found that the following criteria should be satisfied for effective treatment of living tissues and cells, in particular, hard tissue such as bone.

In the following presentation, the signals shown in FIGS. 5a and 5b constitute the pulses of electrical potential and concomitant current generated by the coil and impressed upon the tissues and/or cells. These pulses have one polarity upon "energization" of the coil (termed herein the "positive" pulse portion and shown as the positive-going portion of the waveform on FIGS. 5a and 5b). These pulses have an opposite polarity upon "de-energization" of the coil (termed herein the "negative" pulse portion and shown as the negative-going portion of the waveforms of FIGS. 5a and 5b). The terms "positive" and "negative" are intended to be relative only, and are used herein only for the purpose of indicating that pulse portions of opposite polarity, with respect to a reference potential level, are involved.

It has been determined that the "positive" pulse portions should bear a predetermined relationship to the "negative" pulse portions in order to modify beneficially and with uniform results the behavior of living tissues and cells. This predetermined relationship has been achieved by the utilization of two different signal modes, as well as combinations thereof.

In Mode 1 (see FIG. 5a), the asymmetrical waveform induced in tissue or cells by the alternate energization and de-energization of an electromagnetic coil is repeated at a frequency such that the overall duty cycle is no less than about 2%. This frequency, in Mode 1, has typically been about 10–100 Hz with duty cycles of 20–30%. The basic relationship for Mode 1 of the respective frequency amplitude content of the "positive" and "negative" pulse portions is as follows: pulse signal should be of a particular shape, namely, each "positive" pulse portion should be composed of at least three segments, e.g., the segments 39, 40 and 41 in FIG. 5a. As noted above, it has been found that a substantially rectangular shaped "positive" pulse signal portion is particularly useful in the treatment of tissue and cells. However, it is possible that other pulse configurations (other than a simple two-segment spike) may be useful. The peak amplitude of the final segment of each "positive" pulse portion, e.g., the potential v2 in FIG. 5a should be no less than about 25% of the peak amplitude of the first segment 39 of the "positive" pulse portion, e.g., the potential v1 in FIG. 5a.

The peak "negative" portion amplitude is denoted by $v_3$ in FIG. 5a. This peak amplitude should be no more than about $\frac{1}{3}$ the peak amplitude of the "positive" pulse portion. The time duration of each "positive" pulse portion (the period that elapses between times $t_1$ and $t_2$ in FIG. 5a) should be no longer than about 1/9 the time duration of the following "negative" pulse portion (the time elapsing between times $t_2$ and $t_3$ in FIG. 5a). Because the treatment system utilizes an electromagnetic coil, the energy of each "positive" pulse portion is equal to the energy of each "negative" pulse portion, i.e., the area in FIG. 5a embraced by the "positive" pulse portions is equal to the area embraced by the "negative" pulse portions. By satisfying the criteria just mentioned, the energy of each "negative" pulse portion is dissipated over a relatively long period of time, and the average amplitude of that negative pulse portion is limited. It has been found that such average negative amplitude should be no greater than about 1/6 the average amplitude of the "positive" pulse portion.

These relationships also ensure that the "positive" and "negative" pulse portions have the proper frequency-amplitude characteristics within themselves and to each other such that a beneficial modification of the behavior of tissues and cells is accomplished.

Besides the relationships just mentioned, it has been found that the average amplitude of the "positive" pulse portion peak potential should be within the range of about 0.0001 to 0.01 volt per centimeter of tissue or cells, corresponding to between about 0.1 and 10 microampere per square centimeter of treated tissue and/or cells (based upon typical cell and tissue resistivities). It has been found that higher or lower pulse potentials will not result in a benefical effect. It has also been found that the duration of each "positive" pulse portion (the time elapsed between times $t_1$ and $t_2$ in FIG. 5a) should be at least about 200 microseconds. If the time duration of each "positive" pulse portion is less than about 200 microseconds, the tissues and cells are not stimulated sufficiently to modify the repair or other processes. From a practical standpoint, the "positive" pulse portion duration should not be greater than about 1 millisecond. It has also been found that the repetition rate of the pulses should be within the range of about 65 to 75 Hz for bone and other hard tissues. Pulse treatments within this range have been found to be particularly effective with reproducible results for tissues and cells of this type. In general, however, pulse repetition rate should be between about 10 and 100 Hz for good results in tissues and cells.

For the treatment of bone disorders, and particularly for the treatment of pseudarthrosis, it has been found that for Mode 1 an optimum induced "positive" pulse signal portion having a peak amplitude of between about 1 and 3 millivolts per centimeter of treated tissue (1 to 3 microamperes per square centimeter of treated tissue and/or cells) with the duration of each "positive" pulse portion being about 300 microseconds and the duration of each of the "negative" pulse portions about 3300 microseconds, and a pulse repetition rate of about 72 Hz, represents a presently preferred and optimum induced pulse treatment as long as the pulse-shape requirements noted above are met. Total treatment times may vary. It is presently believed that pulse-signal treatments for periods each lasting for at least about 15 minutes, with one or more periods of treatment during a prescribed number of days, may be effective in stimulating tissue and cell behavior. A preferred treatment regime using Mode 1 has been found to be a minimum of 8 hrs/day for a period of four months in difficult cases, and two weeks in less difficult cases.

In Mode 2 treatment (FIG. 5b), the asymmetrical waveform induced in tissue or cells by the alternate energization and de-energization of an electromagnetic coil is applied in a pulse-train modality, which contains bursts (pulse groups) of asymmetrical waveforms. Each burst of asymmetrical pulses has a duration such that the duty cycle of the burst portion is no less than about 1%. The burst frequency has typically been about from 5–50 Hz.

The basic relationships for Mode 2 of the respective frequency-amplitude content of the "positive" and "negative" pulses within the burst section of the pulse train are as follows: each "positive" pulse portion should be composed of at least three segments, e.g., the segments 39', 40' and 41' in FIG. 5b. For this mode, it has also been found that a substantially rectangular shaped "positive" pulse-signal portion is particularly useful in the treatment of tissues and cells. However, it is possible that pulse configurations other than a simple two segment spike may be useful. The peak amplitude of the final segment of each "positive" pulse portion, e.g., the potential v2 in FIG. 5b, should be no less than about 25% of the peak amplitude of the first segment 39' of the "positive" pulse portion, e.g., the potential v1 in FIG. 5b.

Figure 6:
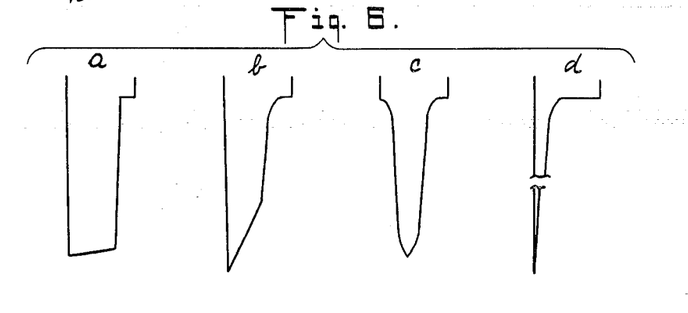
FIG. 6 shows alternative forms of negative pulse portions for Mode 2 treatment.

The peak "negative" amplitude is denoted by v3 in FIG. 5b. This "negative" peak amplitude should be no more than about 40 times the "positive" peak amplitude (in this case v1). This requirement may be met by utilizing "negative" pulse portions having several different waveshape forms, e.g., substantially rectangular, trapezoidal with exponential decay, bell-shaped, or single-spike with exponential decay, as in representative waveforms a, b, c and d in FIG. 6.

The duration of each "positive" pulse portion (the time that elapses between time $t_1$ and $t_2$ in FIG. 5b) should be at least about 4 times the duration of the following "negative" pulse portion (the time that elapses between times $t_2$ and $t_3$ in FIG. 5b). As noted above, since the treatment system utilizes an electromagnetic coil, the energy of each "positive" pulse portion is equal to the energy of each "negative" pulse portion, i.e., the area in FIG. 5b embraced by the "positive" pulse portions is equal to the area embraced by the "negative" pulse portions.

The pulse-repetition rate of the pulses within the burst segment of the Mode 2 pulse train (the time elapsing between times $t_1$ and $t_4$) can be between about 2000 Hz and 10,000 Hz.

The width of the burst segment of the pulse train (the time elapsed between $t_1$ and $t_5$) should be at least about 1% of the time elapsed between $t_1$ and $t_6$.

By satisfying the criteria just mentioned, these relationships also ensure that the "positive" and "negative" pulse portions have the proper frequency-amplitude characteristics within themselves and to each other such that a beneficial modification of the behavior of tissues and cells is accomplished.

Besides the relationships just mentioned, it has also been found that the average magnitude of the "positive" peak potential should be within the range of about 0.00001 to 0.01 volts per centimeter of tissues and/or cells (between about 0.01 and 10 microampere per square centimeter of treated tissue and/or cells).

It has been found that higher or lower pulse potentials will not result in a beneficial effect on tissues and/or cells. It has also been found that the duration of each "positive" pulse portion in the burst segment of the pulse train (i.e., the time elapsed between $t_1$ and $t_2$ in FIG. 5b) should be at least about 1000 microseconds. It has also been found that the repetition rate of the burst segment should be within the range of about 5–15 Hz for bone and other hard tissues.

Each negative-pulse portion within the burst segment of the pulse train should be of a duration no greater than about 50 microseconds and of an average amplitude no greater than about 50 mv/cm of treated tissue and/or cells (about 50 microamperes per square centimeter of treated tissue and/or cells).

For the treatment of bone disorders, and particularly for the treatment of pseudarthroses and non-unions, it has been found that an optimum induced "positive" pulse signal portion having a peak amplitude of between about 1 and 3 millivolts/centimeter of treated tissue (i.e., 1 to 3 microamperes per square centimeter of treated tissue and/or cells), with the duration of each "positive" pulse portion being about 200 microseconds, and the duration of each of the "negative" pulse portions being about 30 microseconds, and a time elapsed between times $t_3$ and $t_4$ of FIG. 5b of 10 microseconds, and a pulse repetition rate of about 4000 Hz, and a burst segment width of about 5 milliseconds, and a burst repetition rate of about 10 Hz, represents a presently preferred and optimum induced pulse treatment in bone for Mode 2, as long as the pulse requirements noted above are met.

It is also believed that a single asymmetrical pulse as described in the burst segment of Mode 2 can be employed at a repetition rate similar to that used in Mode 1 for beneficial modification of tissue growth and repair.

Treatment of living tissues and cells by the above methods herein, in particular for hard tissue such as bone, has demonstrated an increased repair response and generally uniform results have been attained throughout all patient and animal treatments. Particularly beneficial results have been obtained in the cases of treatment of pseudarthrosis in which a bone union has been achieved following previous unsuccessful attempts by other treatment methods and in which amputation has been discussed as a possible alternative to regain function.

In practice, it is believed desirable to utilize as large a coil "window" as possible and to position the coil such that an adequate flux density is impressed upon the tissue and/or cells being treated. As is known, a time-varying magnetic field induces a time-varying voltage field orthogonal to it. That is, the geometry of the magnetic-field lines determines the geometry of the induced-voltage field. Because a relatively uniform induced voltage field is desired, the geometry of the magnetic-field lines should be as uniform as possible, which may be achieved by rendering the size of the coil relatively large with respect to the area under treatment. At this particular time, it is not believed that there need be a particular orientation between the magnetic-field lines and the tissue and/or cells being treated.

It is believed that the uniformity of the induced-voltage field possible through electromagnetic treatment is responsible in many respects for the good treatment results which have been obtained, in distinction to the non-uniform fields which may and probably do result with other types of treatments, for example, utilizing electrostatic fields or by the creation of a potential gradient through the use of electrodes implanted within or on tissues or cells. In particular, an induced voltage field is present in a vacuum as well as in a conducting medium or an insulator. The field characteristics will in general be the same (within one percent) in these three cases, except in the case for which an induced current flow is sufficiently great to create a back electromotive force to distort the magnetic field lines. This condition occurs when the conducting medium has a high conductivity, e.g., a metal, and is large enough to intercept a substantial number of magnetic-field lines. Living systems, i.e., tissue and/or cells, are much less of a conductor than a typical metal (generally by at least $10^5$, i.e., five orders of magnitude). Because of these considerations, the geometry of the magnetic field present in tissue and/or cells is undisturbed and remains unchanged as the tissue and/or cell growth process continues. Thus, with non-invasive electromagnetic treatment, it is believed that the potential gradient that is produced within the tissue and/or cells is constant regardless of the stage or condition of the treatment.

Such uniformity of induced potential is virtually impossible to be achieved through the use of implanted electrodes or by electrostatic coupling or by a transformer coupled to electrodes, or by implanted coils coupled to electrodes. Since these latter types of treatments are dependent upon conductivity, which will vary within tissue and/or cells, the induced potential gradient will not be constant as the condition of the tissue and/or cells changes. Additionally, at any particular time within tissue and/or cells, individual localities of the material being treated will have different conductivity characteristics, which will result in differing potential gradients throughout the material treated.

For these reasons, it is believed that a surgically non-invasive electromagnetic treatment of tissue and/or cells is greatly preferable to electrical treatment by other means.

Regarding typical coil parameters, it is believed that for typical bone breaks, coil windows of about $2.0'' \times 2.75''$ (for an adult) and $2'' \times 1.5''$ (for a child) are suitable. The wire employed in the coils may be B&S gauge 12 copper wire that is varnish-coated to insulate the turns one from another. Coils of about 60 turns for an adult and 70 turns for a child seem to be suitable. For treatments in the oral cavity, coil sizes would be correspondingly smaller.

It is believed that the inductance of the treatment coil should be between about 1–5000 microhenries, and preferably between about 1000 and 3000 microhenries, with sufficiently low resistance (e.g., $10^{-2}$ to 1 ohm) and a high input coil driving signal between about 2 and 30 volts, to induce the appropriate pulse potential in the tissue and/or cells treated. The lesser the inductance of the treatment coil, the steeper the slope of the curves 40 and 40' as shown in FIGS. 5a and 5b; the greater the inductance, the flatter or more rectangular is the "positive" pulse that is produced.

The monitoring of the induced potential may be by actual electrodes making contact with the tissue and/or cells being treated or by use of a pickup coil positioned adjacent to the treatment coil 22 at a distance corresponding to the distance of the material under treatment from the coil. A typical pickup coil that has been employed is circular, about one-half centimeter in diameter, with about 67 to 68 turns of wire. The potential developed by the coil is divided by the length of the wire (in centimeters) to provide an induced voltage per centimeter number that is the same as the volts per centimeter induced in the tissues and/or cells under treatment.

A typical treatment utilizing a coil having a "window" $2'' \times 2.75''$ and 60 turns of number 17 gauge wire, including a diode at the coil such as the diode 27 in FIG. 3, produced the following induced voltages in a pickup coil*, for the pulse times (in microseconds) as follows (voltages and times are with reference to the waveform of FIG. 5):

*These voltage values may be translated into millivolts per centimeter of tissue, by dividing by a factor of substantially 10.

| Induced Voltage | v1 | v2 | v3 | $t_1-t_2$ | $t_2-t_3$ |
|---|---|---|---|---|---|
| Maximum (at face of treatment coil) | 22 | 17 | 3.7 | 300 | 4200 |
| ⅜" from face of treatment coil | 15 | 11.5 | 2.5 | 300 | 4200 |
| 1¼" from face of treatment coil | 6.0 | 4.2 | 1.0 | 300 | 4200 |

The use of pulsing electromagnetic fields to control bone formation in a variety of conditions, now, is on a sound experimental and clinical basis. Thus far, the developments have had application in treating successfully congenital and acquired pseudarthrosis and fresh fractures in humans, increasing the rate of fracture and reactive periostitis repair in animals, and reducing bone loss in disuse osteoporosis of long bones. Success with the method hinges on the discovery of pulse patterns with specific time-frequency-amplitude relationships as outlined above.

EXAMPLES

In order to demonstrate efficacy, the utilization of direct inductive coupling of electromagnetically induced pulsing voltages and concomitant current via Modes 1 and 2 and combinations thereof for hard tissue growth and repair was initially applied in cases of congenital and acquired pseudarthrosis. In a group of patients, only individuals who had been treated previously by one or more unsuccessful surgical attempts (grafting, internal fixation) were accepted. For most of these patients, amputation had been recommended by at least one qualified orthopedist. Throughout this study, the necessity of pulse specificity was illustrated again and again. For example, when lack of ossification was the primary problem (usually the case for congenital pseudarthroses), Mode 1 treatment was utilized with final functional bony union occurring only when the parameters of the pulse corresponded to those given above. On the other hand, when lack of bony matrix was the primary problem, Mode 2 treatment was employed in order to achieve the production of collagen which is the primary supporting protein in bone structure. Since protein production and ossification are two completely different steps in bone formation, the highly selective nature of each of the signals utilized in Modes 1 and 2 could be synergistically combined when neither matrix production nor ossification were present in a given patient's treatment history. Thus, a combination of Modes 1 and 2 was utilized with benefit in this type of situation.

In the case of congenital pseudarthroses, the typical patient is between one and ten years of age. The afflicted part is normally the distal tibia of one extremity. The patients were presented with an average of three prior unsuccessful surgical procedures and had the condition for an average of 5 years, and all were candidates for amputation.

The treatment of such a patient was normally carried out using Mode 1 treatment regime since the primary problem was due to a lack of ossification in the affected area.

The patient is prescribed the appropriate equipment by the attending orthopedic surgeon and carries out his treatment on an out-patient basis. Treatment time is typically 12 to 16 hours a day for about an average of 4 months.

Some 20 of this type of disorder have been treated to date with successful ossification achieved in approximately 90% of the treated individuals.

For acquired pseudarthrosis, either traumatic or operative, patients are mostly adults and had an average number of three failed operations and an average of 2.5 years from onset of non-union. Amputation had been discussed for seventy percent of these individuals. Since in some cases the primary problem was lack of bony matrix, typically visible radiographically as gaps in the bone of more than 2 mm in the fracture site, such a patient was treated commencing with Mode 2 modality. When it was thought that sufficient non-ossified bony matrix was present, Mode 1 modality was employed to gain rapid immobilization of the fracture site.

Because of the particular pathology of several patients in this group, a combination of Modes 1 and 2 was employed with this treatment being specifically Mode 2 followed by Mode 1. As in the case of congenital pseudarthrosis, the proper equipment was prescribed by the attending orthopedic surgeon and treatment was performed on an out-patient basis. Treatment time is typically 10-14 hours/day for periods ranging from 3 to 9 months.

Some 30 of this type of disorder have been treated to date with successful bony union observed in 75% of the treated individuals.

These clinical results clearly demonstrate that once the particular pathology of a bone disorder is diagnosed it can be selectively beneficially treated by the application of properly encoded changes in electrical environment.

Similar findings have been obtained from a study of bilateral femoral and radial osteotomies in 160 rats. These animals were divided into two major groups; field exposed and control for an interval of 14 days after operation. Following sacrifice, the extent of fracture repair was judged on the basis of X-ray and histologic evaluation, coupled with non-destructive mechanical testing. These animal models were employed to evaluate the effectiveness of treatment modalities of Modes 1 and 2 and combinations thereof. Generally, when the osteotomy gap was less than 1.0 mm, a Mode 1 signal was effective since very little bony matrix was required for solidification. On the other hand, for wider osteotomies, substantially increased matrix production was observed over control animals when Mode 2 was employed. A combination of Modes 1 and 2 was employed in the latter case to obtain a stiffer repair site for an equivalent treatment time.

This was further evaluated by the response of these bones to mechanical testing. This was performed by subjecting the bond of the rats following sacrifice to cantilever loading at various deformations in accordance with the testing procedures described in "Acceleration of Fracture Repair by Electromagnetic Fields. A Surgically Non-invasive Method" by C. A. L. Bassett, R. J. Pauluk and A. A. Pilla, published on pp. 242-262 of the *Annals of The New York Academy of Sciences* referenced above. The specimens were deformed in the antero-posterior, lateral-medial, postero-anterior, medial-lateral and again the antero-posterior positions.

The average response of a femur to this test at a deformation of 0.05 inch is shown in Table I as follows:

TABLE I

| Mechanical Load Values In Electrical Stimulation of Artificial Osteotomies In Adult Female Rat Femur | |
|---|---|
| Stimulation | Load at 0.05 in. Deformation |
| Control (untreated) | 42 gms. ± 5.2 gms. |
| Mode 1 Signal (FIG. 5$_a$) | 580 gms. ± 65 gms. |

In addition to radiographic and mechanical evidence of the effectiveness of the signal employed, histologic evidence further attests to this effectiveness.

Hemotoxylin and eosin stained longitudinal specimens show a much higher degree of maturation for the Mode 1 signal than in the control case.

For wider osteotomy gaps, treatment times of fourteen days showed that the active animals had a significantly larger callus than controls. Histologic evidence shows that the increase is at least 150% over controls.

Limited tooth extraction studies have been performed and show that pulses of the Mode 1 type may have a highly beneficial effect on the rate of healing and on bone loss in the oral cavity. The latter effect in the oral cavity is particularly important for the maintenance of mandibular and maxillar crestal bone height, a very important factor for implant fixation.

These observations all point to the fact that electromagnetic fields with highly specific pulse characteristics can be non-invasively inductively coupled to biological systems to control cell behavior. In the initial application of these principles, effects on bone cells have been investigated. Other biological processes, however, may eventually be proven to be controlled by similar techniques, e.g., malignancy, neuro-repair, inflammatory processes and immune response, among others.

In summary, it is believed that a unique electromagnetic and surgically non-invasive treatment technique has been discovered. Induced pulse characteristics appear to be highly significant, especially those relating to the time-frequency-amplitude relationships of the entire pulse or pulse sequence. It is believed that selection of particular time-frequency-amplitude relationships may be the key to successful treatments of varying cellular behavior in a variety of tissues.

Throughout the specification for Mode 1, a preferred pulse repetition rate of between about 65 and 75 Hertz had been specified for bone and other hard tissue. The exact limits of the pulse-repetition rate are not known for all types of tissues and cells. It is believed that preferred operating ranges will vary depending on the tissue and cell type. Positive results have been obtained, for example, in soft-tissue treatment at 20 Hertz.

It will be appreciated that the methods and apparatus described above are susceptible of modification. For example, while FIGS. 1 and 2 illustrate a treatment unit which may be strapped to the leg, treatment units incorporated in casts, e.g., may be employed. Further, treatment may be carried out by use of one or more coils of varying shapes positioned adjacent to tissue and/or cells to be treated; in fact, some treatments of humans have involved coils positioned upon opposite sides of a bone break, as suggested by legend reference to the plural at 22 in both FIG. 4 and FIG. 5, and as described more fully in our said copending application Ser. No. 887,485.

In order to consider further employments and refinements of the methods and apparatus described above, certain generalized observations are believed to be justified by experience to date in use of the described Mode 1 and/or Mode 2 waveforms, electromagnetically coupled as above described. Such waveforms will sometimes be referred to as "encoded" or "coded" because waveshape, pattern and their variation, implicit in use of the words "variable" and "control" in legends at 30-34-35-36-37 (FIGS. 4 and 5), appear to be increasingly significant in achieving newly discovered therapeutic benefits from the invention.

First, the cell and/or tissue interface (with the applied field) is selective in its response to pulse width; for example, no biological effect has been observed for pulse widths less than about 50 microseconds, at the indicated relatively low induced-voltage levels, neither is there any observable heat development at the cell and/or tissue under such conditions.

Second, repetition rate is a key factor if therapeutically beneficial results are to be obtained with pulse excitation, coded as above described; in other words, pulse-repetition rate is important if the interface is to perceive a net change (more or less charge).

Third, any given cell (and its surface) must be in a potentiated condition (or state) if it is to act in response to the applied code. Conditioning (potentiating) can be the product of a natural trauma, as for example when cells discharge more potassium ions ($K^+$) or calcium ions ($Ca^{++}$) into their microenvironment. Conditioning may also be the product of an artificial factor, exemplified by injection of a new species (e.g. a drug) into the region to be treated, in which case the described pulse signals will act synergistically (or non-synergistically), depending upon the particular artificial situation.

Fourth, cells in different states require different signal codes if their interfaces are to perceive a net change.

Fifth, body response to an injury results in cells in different states; indeed, in different cells, for certain kinds of injury.

In view of the foregoing considerations, and in accordance with the invention, the range of therapeutic benefit from the above-described method and apparatus can be extended by varying one or more elements of the applied pulse code, in the course of a given body treatment. And, as currently envisioned by us, it is the pulse width and/or the repetition rate and/or the amplitude which should be made subject to a predetermined pattern or program of variation. FIGS. 7 to 11 are specifically concerned with achievement of such variation in methods and apparatus of the present character.

Figure 7:
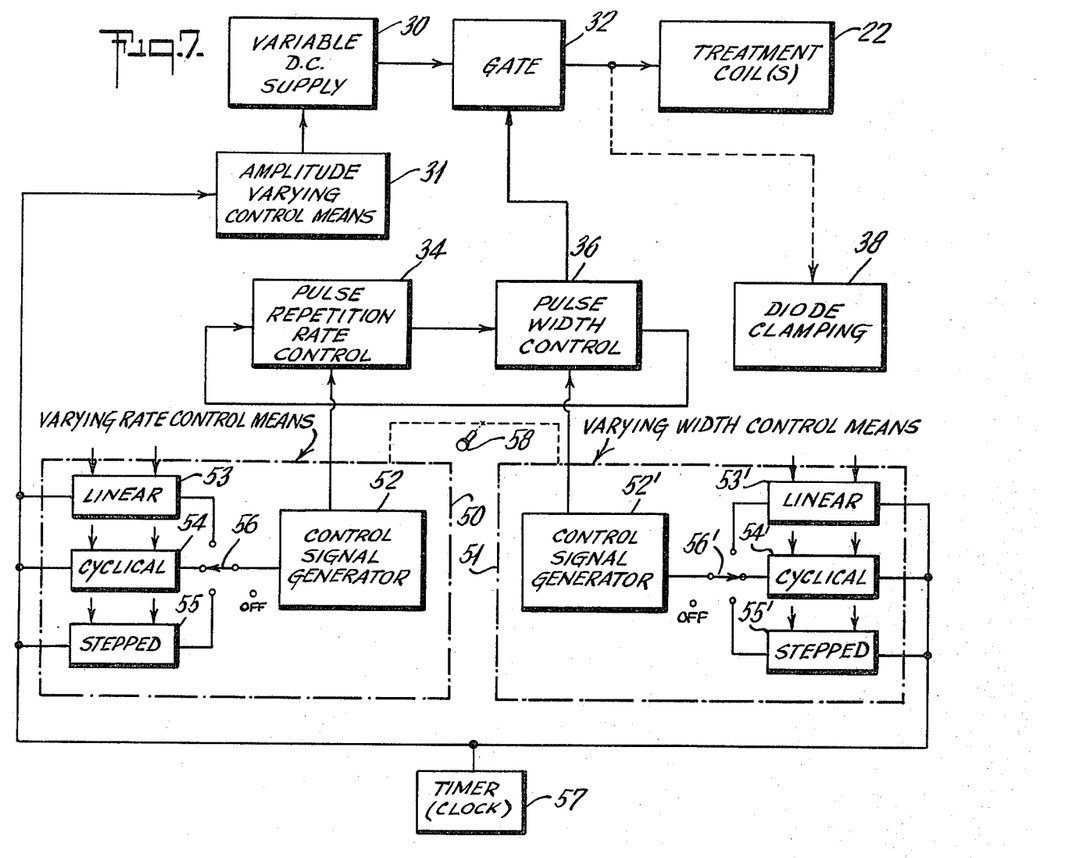

The circuit of FIG. 7 will be recognized as a Mode-1 circuit, being a refinement of FIG. 4, and corresponding components are identified by the same reference numbers. The refinement comprises connection of varying-rate control means 50 to the pulse-repetition-rate control 34, so as to provide a predetermined pattern of varying pulse-repetition rate at the output of means 34. In analogous manner, varying-width control means 51 is connected to the pulse-width control 36, so as to provide a predetermined pattern of varying pulse width at the output of means 36. Still further analogously, pulse amplitude is made the subject of selectively programmable controlled variation, as suggested by legend at 31 in application to the variable DC supply 30. The gate 32 is thus controlled for Mode-1 signal supply to coil means 22 wherein not only the width and the repetition rate but also the amplitude of Mode-1 pulses (e.g. as in FIG. 5a) are controllably variable in the course of a given treatment.

Figure 8:
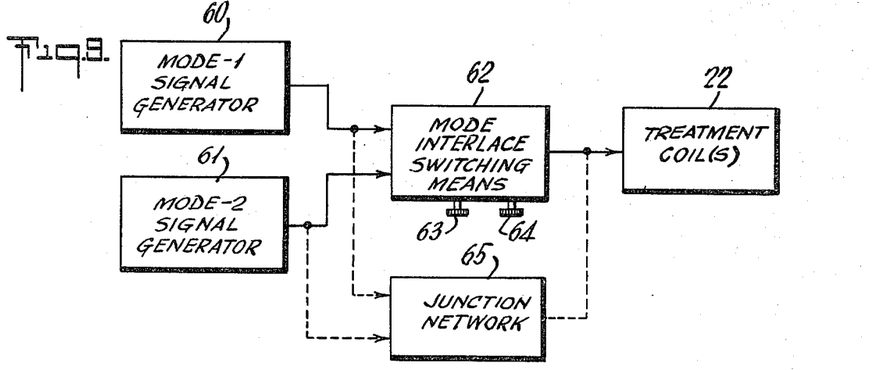

In the case of the varying-rate control means 50, a signal generator 52 is subject to controlled operation in accordance with a selected one of a plurality of different functions indicated by different illustrative legends at 53-54-55, selection being made by switch means 56 having an "OFF" position in the event that a particular treatment calls for no variation in pulse-repetition rate. Multiple arrows at each of the different function circuits 53-54-55 will be understood to suggest two of a plurality of selectively available controls, appropriate to selection of particular parameters for the particular control; two such selectively available controls for each of circuits 53-54-55 may thus determine selected lower and upper limits of the repetition-rate variation to be provided by the particular circuit, and a further such selectively available control for each of circuits 53-54-55 may determine the speed with which pulse-repetition rate is to be changed and the frequency with which it is to change within the selected limits of pulse-repetition rate. Similar legends and primed notation as to the components of the varying-width control means 51 will be understood to suggest its basic signal-generating similarity to the control means 50, it being understood that limits of parameter-value selection at 51 are as appropriate for pulse-width control at 36. A single timing means or clock 57 is shown connected for synchronously timed operation of all the function circuits 53-54-55-53'-54'-55' and at 31.

Generally speaking, the range of pulse width and the range of repetition rates of Mode-1 pulses produced by the circuit of FIG. 7 accord with ranges discussed above for Mode 1 operation. And the rate-varying capability of circuit 50, the width-varying capability of circuit 51, and the amplitude-varying capability of control means 31 accommodate the full above-stated ranges, it being understood that the selectively operable elements (as at 53-54-55) enable selection of automatically scanned lesser ranges of repetition-rate variation and the speed or other nature of repetition-rate variation, while selectively operable elements (as at 53'-54'-55') enable corresponding selection of automatically scanned lesser ranges of pulse-width variation. For example, the selected rate of variation of pulse width may be smoothly and linearly variable (circuit 52' selected) over the course of selected time representing a minimum, up to 24 hours, as for the unusual circumstance of a full day of treatment. And a dashed-line adjustable control interconnection 58 between circuits 50-51 will be understood to suggest a single adjustment of Mode-1 duty cycle, ranging from a 1:1 or 50% duty cycle (wherein the pulse-repetition rate and the pulse-width are such as to achieve a dwell between pulses equal to the pulse duration), to a 1:50 or 2% duty cycle (wherein the period between successive pulses is fifty times the duration of each applicable pulse).

FIG. 8 will be recognized as a Mode-2 circuit similar to FIG. 5, the circuit of FIG. 8 being identified by reference numbers and interconnections already described, and the function-varying techniques of FIG. 7 are again employed. Thus, the varying-rate control means 50 is timer (i.e. program) coordinated and provides a rate varying control signal to the pulse-repetition rate control means 34, while the varying-width control means 51 performs similarly for the pulse-width control 36 and a program of amplitude variation is selectively available at 31. Still further, a second varying-rate control means 50' and a second varying-width control means 51' are connected to respectively determine variation in Mode-2 burst-repetition rate (i.e. how often and at what varying rate the Mode-2 bursts are repeated) and variations in the width of the Mode-2 bursts, as will be understood. Finally, the adjustable duty-cycle control connection 58 in FIG. 8 will be understood to determine duty cycle within the burst phase of Mode-2 operation, while a similar duty-cycle control connection 58' determines duty cycle of the burst with respect to the instantaneous rate of burst repetition (i.e. period from burst to successive burst).

Figure 10:
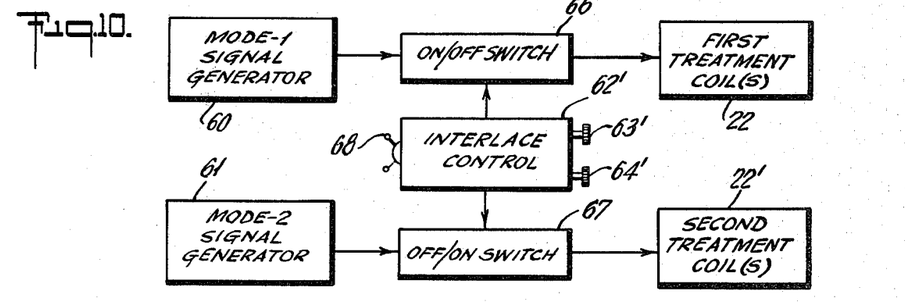
Figure 11:
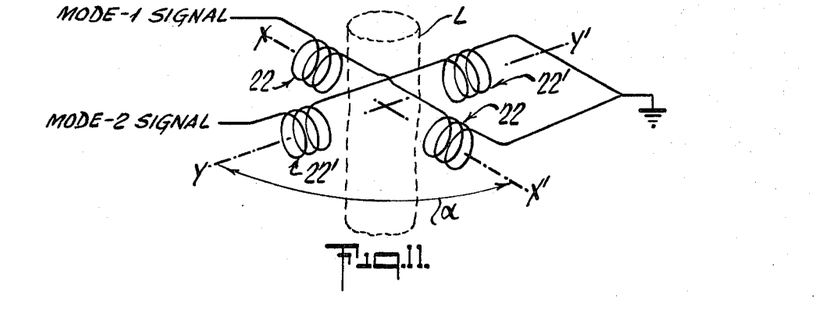

The circuit means of FIGS. 9 to 11 illustrate various ways in which different excitation-signal patterns (e.g. Mode-1 and Mode-2 signals) may be combined for use in the course of a given treatment period for a particular patient, and the legends at 60-61 will be understood respectively to identify FIG. 4 (FIG. 7) apparatus and FIG. 5 (FIG. 8) apparatus, as may be indicated for the particular patient's therapy.

In the arrangement of FIG. 9, the Mode-1 and Mode-2 generator outputs are both supplied to the single treatment coil or coils 22, already described. Solid-line connections via switching means 62 enables the Mode-1 signals to be time-interlaced with Mode-2 signals in their application to coil(s) 22. Separate selectively operable adjustment-knob means 63-64 indicate that the time of each period of Mode-1 signal pulsing to coil(s) 22, and the time of each Mode-2 period interlaced therewith, may be independently adjusted as desired for a particular patient, the automatic interlace-switching function being cyclically repeated for the time duration of the particular treatment. Dashed-line interconnection of Mode-1 signals and Mode-2 signals to coil(s) 22 independently of interlace switching at 62 is to be understood to indicate that, if desired in certain cases, the Mode-1 and Mode-2 signals can be concurrently supplied to coil(s) 22 (via a suitable junction network 65), i.e. without the alternating succession of interlaced switching connections otherwise available via means 62. Network 65 will be understood to include signal isolating components such as diodes to assure against feed of Mode-1 signals to generator 61 (or Mode-2 signals to generator 60), all to the end that such signals (i.e. both Mode-1 and Mode-2 signals) are supplied only to coil(s) 22, whenever their concurrent (as distinguished from their interlaced) supply is selected.

The circuit of FIG. 10 is essentially what has been described in connection with FIG. 9, except that in FIG. 10 Mode-1 generator output is supplied (via switch means 66) exclusively to first treatment coil(s) 22, while Mode-2 generator output is supplied (via switch means 67) exclusively to second treatment coil(s) 22', both coil(s) 22 and coil(s) 22' being applied to the same patient for a given period of treatment. The coil(s) 22 and 22' may be applied to different body locations so as to establish their respective electromagnetic fields at quite different body regions, for example through a leg region via coil(s) 22 and through an arm region via coil 22'; however, the arrangement of FIG. 11 illustrates that the coil(s) 22 and the coil(s) 22' may be applied in angularly spaced array about a given limb L and at substantially the same longitudinal location along the limb. In the case of FIG. 11 there are two coils 22 mounted to diametrically opposite sides of the limb L, coils 22 being connected for flux-aiding and oriented for magnetic flux-development of Mode-1 signals along the axis X-X' through the afflicted region; similarly, two coils 22' have flux-aiding connection for development of Mode-2 signals along the axis Y-Y' through the afflicted region but at angular offset $\alpha$ from the axis X-X' of Mode-1 signal application.

Returning to FIG. 10, the switch means 66-67 are seen to be under synchronizing control of an interlace program provided by suitable time-sharing means 62', with separately adjustable means 63'-64' for selection of the desired time interval for each period of one of its phases (e.g. Mode-1 signal phase), and of the desired time interval for each period of its other phase (e.g. Mode-2 signal phase) of operation of the respective switch means 66-67. The legends "ON/OFF" at 66 and "OFF/ON" at 67 indicate that during interlace-synchronization control by means 62', switch means 66 is "ON" while switch means 67 is "OFF", and switch means 66 is "OFF" while switch means 67 is "ON". A manual control 68 determines whether or not the described interlace function is to be provided by means 62', and it will be understood that for the "interlace de-activated" position of control 68, the means 62' effectively sets both switch means 66-67 to their respective "ON" states, thereby concurrently applying both Mode-1 and Mode-2 signals to the patient.

It will be seen that the described apparatus of FIGS. 7 to 11 provides specific illustration of various means whereby the means 30-34-35-36-37 of FIGS. 4 and 5 may respectively be caused to vary their control of different code parameters, in the Mode-1 and/or Mode-2 application of therapeutically beneficial signals to an afflicted body region under treatment. Encoding of applied signals has been found to be specific for a particular cell or tissue function. But a non-homogeneous cellular and/or tissue environment exists in many trauma and developmental situations; indeed, the electrochemical micro-environment existing under such conditions appears to provide a natural source of electrochemical information to control the cellular activity necessary for an adequate progression to a more normal state. This electrochemical information can also be supplied by chemically modifying the micro-environment of cells by injecting or applying specific ions, drugs, hormones, etc.; cells respond to this micro-environment by the interaction of charged species at their interfaces and junctions, and the charged-species availability varies with the condition of the intercellular environment. The present invention provides the method and means analogously and with more effective control to selectively change and operate upon the intercellular environment, in the realistic circumstance that at a given time different cells are in different states and are necessarily subject to electromagnetic action only via different specifically coded signals.

The particular code that is beneficially effective for a specific cellular response thus depends on the state of each cell and the state of its micro-environment. In many situations of a repair or development function, the cellular population and the micro-environment are heterogeneous and change with time; and by providing for application of encoded pulsative signals wherein the code is programmed to vary in specific time-related sequences, the invention provides the means for optional synergism of interface specific current, micro-environment, and cellular state. Still further, the invention may be viewed as providing for the concomitant application of a specifically programmed chemical change in the cellular micro-environment, by applying encoded pulsating currents whose code is programmed to vary in specified time-related sequences.

From what we have been able to observe and deduce to date, a net biological effect resulting from the application of interface-selective currents appears to occur only when the cell and/or tissue exists in what may be termed a potentiating condition. This potentiating condition can be achieved by both natural and artificial means. Since the action of interface-selective pulsating currents depends upon a specific net change in the charged-species interactions at cell functions and surfaces, the proper sequence of net interfacial changes required for each cell in each of its states and for each of its micro-environmental conditions, can be achieved by a programmed variation of one, two, or all three of the indicated variables: pulse width, pulse-repetition rate, and amplitude, e.g. pulse width and/or repetition rate for a given set of amplitude conditions. And the legend "TIMER" applied at 57 in FIGS. 7 and 8 will be understood to be broad enough to include programming means wherein one or more of the varying control means 31-50-51 is itself program-controlled to change its varying control of pulse-width, pulse amplitude and/or repetition rate in accordance with a preset program of time-variation which changes in the course of a given treatment.

While the lower limit of voltage and/or current amplitude was earlier determined to be at or about the 0.0001 volt level (corresponding to about 0.1 microampere per square centimeter) stated above, there is now reason to believe that, in the presence of certain applied chemical additives (for example, drugs, hormones, salts or other ion sources), the minimum voltage and/or current levels to achieve therapeutically beneficial results with the apparatus and method of the invention is thereby reduced by about one order of magnitude, so that the minimum voltage and/or current levels are more accurately stated as 0.00001 volt, corresponding to about 0.1 microampere per square centimeter of cells and/or tissue.

Similarly, the minimum pulse width may be reduced from the above-stated minimum, to at least as short an interval as 100 microseconds, with beneficial use of pulse widths in the range 100 microseconds to substantially 250 milliseconds, and pulse-repetition rates in a range up to substantially 10,000 pulses per second.

What is claimed is:

1. An electromagnetic body-treatment device for surgically non-invasive modification of the growth, repair and maintenance behavior of living tissues and cells by a specific and selective change in electrical environment, comprising electromagnetic means including a portion adapted for positioning alongside an afflicted body region to be treated, said electromagnetic means including electrical-coil means for establishing via said portion a flux path through the body region, means for electrically exciting said coil means with a succession of low-voltage unidirectional asymmetrical pulses, said pulses having a minimum width characteristic of at least 100 microseconds and a minimum pulse-repetition-rate characteristic of at least one per second and a minimum low-voltage characteristic of at least 0.00001 volt per centimeter of treated tissue and/or cells corresponding to about 0.01 microampere per square centimeter of treated tissue and/or cells, and function-varying means operatively associated with said electrical-excitation means for varying at least one of said characteristics in the course of a body treatment and within a range of variation extending above the stated minimum value thereof.

2. The treatment device of claim 1, in which said function-varying means is operatively associated with said electrical-excitation means for varying at least two of said characteristics within a range of variation above their respective stated minimum values.

3. The treatment device of claim 2, in which said function-varying means comprises a first function-varying circuit operatively associated with said excitation means to determine variation of said pulse-repetition-rate characteristic above the stated minimum value thereof, and a second function-varying circuit operatively associated with said excitation means to determine variation of said pulse-width characteristic above the stated minimum value thereof.

4. The treatment device of claim 3, in which said function-varying means further comprises a third function-varying circuit operatively associated with said excitation means to determine variation of said low-voltage characteristic above the stated minimum value thereof.

5. The treatment device of claim 3, including a synchronizing connection between the respective function-varying circuits to maintain a predetermined duty-cycle relation between pulse width and pulse-repetition-rate in the course of varying pulse width and pulse-repetition-rate.

6. The treatment device of claim 5, in which said synchronizing connection includes selectively operable means for changing said duty-cycle relation.

7. The treatment device of claim 5, in which the duty-cycle relation is substantially constant.

8. The treatment device of claim 5, in which the duty-cycle relation is in the range 1:1 to 1:50.

9. The treatment device of claim 2, in which said function-varying means includes program-timing means involving differently varying control of at least one of said two characteristics in the course of a given single timed program of variation.

10. The treatment device of claim 1, in which said function-varying means is associated with said excitation means to enable variation of pulse-repetition-rate within a range up to substantially 10,000 pulses per second.

11. The treatment device of claim 1, in which said function-varying means is associated with said excitation means to enable variation of pulse width within a range up to substantially 250 milliseconds.

12. The treatment device of claim 1, in which said function-varying means is associated with said excitation means to enable variation of voltage amplitude within a range up to 0.1 volt per centimeter of treated tissue and/or cells.

13. An electromagnetic body-treatment device for surgically non-invasive modification of the growth, repair and maintenance behavior of living tissues and cells by a specific and selective change in electrical environment, comprising electromagnetic means including a portion adapted for positioning alongside an afflicted body region to be treated, said electromagnetic means including electrical-coil means for establishing via said portion a flux path through the body region, first and second means for electrically exciting said coil means with first and second different successions of low-voltage unidirectional asymmetrical pulses, said pulses having a minimum width characteristic of at least 100 microseconds and a minimum pulse-repetition-rate characteristic of at least one per second and a minimum low-voltage characteristic of at least 0.00001 volt per centimeter of treated tissue and/or cells corresponding to about 0.01 microampere per square centimeter of treated tissue and/or cells, one of said excitation means providing a coil-excitation output characterized by a first mode of succession of asymmetrical pulses selected to produce a first electro-magnetically induced therapeutic result, and the other of said excitation means providing a coil-excitation output characterized by a second and different mode of succession of asymmetrical pulses selected to produce a second electro-magnetically induced therapeutic result, and function-varying means operatively associated with said first and second electrical excitation means for varying at least one of said characteristics in the course of a body treatment and within a range of variation extending above the stated minimum value thereof.

14. The treatment device of claim 13, in which said first and said second excitation means are both connected to said coil means for concurrent application of both said modes.

15. The treatment device of claim 13, in which the connection of said first and second excitation means to said coil means includes control means for interlacing the coil-means connection of one of said excitation means in alternating time sequence with the coil-means connection of the other of said excitation means.

16. The treatment device of claim 13, in which said coil means is one of two generally similar coil means each with its own excitation means adapted to establish first and second separate magnetic-flux paths through different body-treatment regions, the first excitation means being operatively connected to one coil means for excitation via one of said paths and the second excitation means being operatively connected to the other coil means for excitation via the other of said paths.

17. The treatment device of claim 16, in which said two coil means are so compatably adapted to each other as to enable said paths to be established through a body region common to both paths.

18. The treatment device of claim 17, wherein the compatable adaptability of each of said coil means to the other is such as to permit establishment of each flux path essentially straight through a region between opposite sides of the body portion under treatment, said paths intersecting substantially at the afflicted body region.

19. The treatment device of claim 16, in which interlace-control means is operatively associated with said first and second excitation means for interlacing control of a period of first-mode pulse excitation of one of said coil means in alternating time sequence with a period of second-mode pulse excitation of the other said coil means.

20. The treatment device of claim 15 or claim 19, in which said interlace-control means includes means for selectively varying the time-sharing period of at least one of said interlaced modes.

21. The treatment device of claim 19, in which said interlace-control means includes selectively operable means for effectively disabling the interlaced coil-means connection of said respective modes, at least one of said excitation means being continuously connected to said coil means while said interlace-control means is effectively disabled.

22. The treatment device of claim 21, in which both said excitation means are continuously connected to said coil means while said interlace-control means is effectively disabled.

23. The method of using an electromagnetic body-treatment device for surgically non-invasive modification of the growth, repair and maintenance behavior of living tissues and cells by a specific and selective change in electrical environment, said device comprising electromagnetic means including a portion adapted for positioning alongside an afflicted body region to be treated, said electromagnetic means including electrical-coil means for establishing via said portion a flux path through the body region, means for electrically exciting said coil means with a succession of low-voltage unidirectional asymmetrical pulses, said pulses having a minimum width characteristic of at least 100 microseconds and a minimum pulse-repetition-rate characteristic of at least one per second and a minimum low-voltage characteristic of at least 0.00001 volt per centimeter of treated tissue and/or cells corresponding to about 0.01 microampere per square centimeter of treated tissue and/or cells, and function-varying means operatively associated with said electrical-excitation means for varying at least one of said characteristics in the course of a body treatment and within a range of variation extending above the stated minimum value thereof; said method comprising selecting a first pattern of asymmetrical pulses to produce a first desired cellular response, selecting a second and different pattern of asymmetrical pulses to produce a second and different desired cellular response, and setting said function-varying means so as to include both said patterns.

24. The method of claim 23, in which said function-varying means is operated for excitation of said coil means in time-interlaced sequential alternation of periods in accordance with said respective patterns.

25. The method of claim 23, in which said function-varying means is operated for excitation of said coil means concurrently in accordance with both said patterns for at least a portion of a given body-treatment.

26. The method of claim 23, in which said function-varying means is operated for excitation of said coil means in a program of pattern variation involving variation of one of said characteristics to produce a plurality of patterns which plurality includes at least one of said patterns and patterns closely akin to the same.

27. The method of claim 23, in which the first pattern has a first duty cycle and the second pattern has substantially the same duty cycle, and said function-varying means is operated to vary pulse width and repetition rate at substantially said duty cycle and in the range between said patterns.

28. The method of claim 23, in which said first pattern has a first duty cycle and the second pattern has a second duty cycle, and said function-varying means is operated to vary pulse width and repetition rate at a substantially uniform rate of change of duty cycle between said patterns.

* * * * *